(12) United States Patent
Leatherman et al.

(10) Patent No.: US 8,008,231 B2
(45) Date of Patent: Aug. 30, 2011

(54) EXTREME ENVIRONMENT SURFACTANT COMPOSITIONS COMPRISING HYDROLYSIS RESISTANT ORGANOMODIFIED DISILOXANE SURFACTANTS

(75) Inventors: Mark D. Leatherman, Elmsford, NY (US); George A. Policello, Ossining, NY (US); Suresh K. Rajaraman, Newburg, NY (US)

(73) Assignee: Momentive Performance Materials Inc., Albany, NY (US)

( * ) Notice: Subject to any disclaimer, the term of this patent is extended or adjusted under 35 U.S.C. 154(b) by 1430 days.

(21) Appl. No.: 11/427,961

(22) Filed: Jun. 30, 2006

(65) Prior Publication Data

US 2007/0087937 A1   Apr. 19, 2007

Related U.S. Application Data

(63) Continuation-in-part of application No. 11/301,707, filed on Dec. 13, 2005, now Pat. No. 7,645,720.

(60) Provisional application No. 60/726,409, filed on Oct. 13, 2005.

(51) Int. Cl.
 *A01N 55/10* (2006.01)
(52) U.S. Cl. ........................................ 504/193; 524/731
(58) Field of Classification Search .................. 504/193; 524/731
 See application file for complete search history.

(56) References Cited

U.S. PATENT DOCUMENTS

| | | | |
|---|---|---|---|
| 3,299,112 | A | 1/1967 | Bailey |
| 5,132,047 | A | 7/1992 | Tanaka et al. |
| 6,211,284 | B1 | 4/2001 | Ishikawa et al. |
| 7,399,350 | B2 | 7/2008 | Rajaraman |
| 7,645,720 | B2 * | 1/2010 | Leatherman et al. ......... 504/363 |
| 2007/0086968 | A1 * | 4/2007 | Leatherman et al. ...... 424/70.12 |
| 2007/0088091 | A1 * | 4/2007 | Leatherman et al. .......... 516/55 |
| 2007/0135308 | A1 | 6/2007 | Leatherman |

FOREIGN PATENT DOCUMENTS

| | | |
|---|---|---|
| EP | 0786515 | 7/1997 |
| EP | 1136515 | 9/2001 |
| WO | 2007/044552 | 4/2007 |
| WO | 2007/044691 | 4/2007 |

OTHER PUBLICATIONS

Greene, Theodora W, "Protective Groups in Organic Synthesis", 1981, John Wiley & Sons, New York, XP002435637 p. 39, last paragraph, p. 44, second paragraph.
XP-002435434—Database CA [Online] Chemical Abstracts Service, Columbus, Ohio, US; Mar. 4 Zhang Zhengcheng et al: "Oligo(ethylene glycol)—functionalized disiloxane: synthesis and conductivity" XP002435434 retrieved from STN database accession No. 2005:183434 abstract and PMSE Preprints, 92, 365-366 Coden: PPMRA9; ISSN: 1550-6703, 2005, Figures 1, 2.
XP-002435637.

* cited by examiner

*Primary Examiner* — Rebecca Prouty
*Assistant Examiner* — Danielle Sullivan
(74) *Attorney, Agent, or Firm* — Dominick G. Vicari

(57) ABSTRACT

Compositions comprising an asymmetric disiloxane surfactant composition comprising a silicone composition comprising a silicone having the formula:

$$MM'$$

where M or M' comprises an alkylpolyalkyleneoxide bearing substituent selected from the group consisting of:

$R^{13}(C_2H_4O)_a(C_3H_6O)_b(C_4H_8O)_cR^{14}$ and
$R^{12}SiR^5R^6(R^{13}(C_2H_4O)_a(C_3H_6O)_b(C_4H_8O)_cR^{14})$ that exhibit resistance to hydrolysis over a wide pH range.

21 Claims, No Drawings

EXTREME ENVIRONMENT SURFACTANT COMPOSITIONS COMPRISING HYDROLYSIS RESISTANT ORGANOMODIFIED DISILOXANE SURFACTANTS

CROSS REFERENCE TO RELATED APPLICATIONS

This application is a Continuation-In Part application of U.S. Ser. No. 11/301,707 filed Dec. 13, 2005 now U.S. Pat. No. 7,645,720 and claims the benefit of U.S. Provisional Application Ser. No. 60/726,409, filed Oct. 13, 2005

FIELD OF THE INVENTION

The present invention relates to extreme environment compositions comprising disiloxane surfactant compositions that exhibit resistance to hydrolysis over a wide pH range. More particularly the present invention relates to such extreme environment compositions having a resistance to hydrolysis between a pH of about 3 to a pH of about 12.

BACKGROUND OF THE INVENTION

The topical application of liquid compositions to the surfaces of both animate and inanimate objects to effect a desired change involve the processes of controlling wetting, spreading, foaming, detergency, and the like. When used in aqueous solutions to improve the delivery of active ingredients to the surface being treated, trisiloxane type compounds have been found to be useful in enabling the control of these processes to achieve the desired effect. However, the trisiloxane compounds may only be used in a narrow pH range, ranging from a slightly acidic pH of 6 to a very mildly basic pH of 7.5. Outside this narrow pH range, the trisiloxane compounds are not stable to hydrolysis undergoing a rapid decomposition.

SUMMARY OF THE INVENTION

The present invention provides for an extreme environment composition useful as an agricultural composition, a personal care composition, a coating composition or a home care composition, said composition comprising a silicone composition comprising a silicone having the formula:

MM' where
$M = R^1 R^2 R^3 SiO_{1/2}$;
$M' = R^4 R^5 R^6 SiO_{1/2}$;
with $R^1$ selected from the group consisting of branched monovalent hydrocarbon radical of from 3 to 6 carbon atoms and $R^7$, where $R^7$ is selected from the group consisting of
$R^8 R^9 R^{10} SiR^{12}$ and $(R^4 R^5 R^6)SiR^{12}$
with $R^8$, $R^9$, and $R^{10}$ each independently selected from the group of monovalent hydrocarbon radicals having from 1 to 6 carbon atoms and monovalent aryl or alkaryl hydrocarbon radicals having from 6 to 13 carbon atoms and $R^{12}$ is a divalent hydrocarbon radical having from 1 to 3 carbon atoms,
$R^2$ and $R^3$ are each independently selected from the group of from 1 to 6 carbon atom monovalent hydrocarbon radicals or $R^1$, with $R^4$ an alkylpolyalkyleneoxide bearing substituent selected from the group consisting of:
$R^{13}(C_2H_4O)_a(C_3H_6O)_b(C_4H_8O)_c R^{14}$ and
$R^{12}SiR^5R^6(R^{13}(C_2H_4O)_a(C_3H_6O)_b(C_4H_8O)_c R^{14})$
where $R^{13}$ is a divalent linear or branched hydrocarbon radical having the structure:
$-CH_2-CH(R^{15})(R^{16})_d O-$
where $R^{15}$ is H or methyl; $R^{16}$ is a divalent alkyl radical of 1 to 6 carbons where the subscript d may be 0 or 1;
$R^{14}$ is selected from the group consisting of H, monovalent hydrocarbon radicals of from 1 to 6 carbon atoms and acetyl where the subscripts a, b and c are zero or positive and satisfy the following relationships:

$2 \leq a+b+c \leq 20$ with $a \geq 2$, and $R^5$ and $R^6$ are each independently selected from the group of monovalent hydrocarbon radicals having from 1 to 6 carbon atoms or $R^4$.

DETAILED DESCRIPTION OF THE INVENTION

As used herein, integer values of stoichiometric subscripts refer to molecular species and non-integer values of stoichiometric subscripts refer to a mixture of molecular species on a molecular weight average basis, a number average basis or a mole fraction basis.

The present invention provides for a disiloxane compound or compositions thereof useful as a surfactant having the general formula:

MM' where
$M = R^1 R^2 R^3 SiO_{1/2}$;
$M' = R^4 R^5 R^6 SiO_{1/2}$;
with $R^1$ a branched monovalent hydrocarbon radical of from 3 to 6 carbon atoms or $R^7$, where $R^7$ is selected from the group consisting of
$R^8 R^9 R^{10} SiR^{12}$ and $(R^4 R^5 R^6)SiR^{12}$
with $R^8$, $R^9$, and $R^{10}$ each independently selected from the group of monovalent hydrocarbon radicals having from 1 to 6 carbon atoms and monovalent aryl or alkaryl hydrocarbon radicals having from 6 to 13 carbon atoms and $R^{12}$ is a divalent hydrocarbon radical having from 1 to 3 carbon atoms,
$R^2$ and $R^3$ are each independently selected from the group of from 1 to 6 carbon atom monovalent hydrocarbon radicals or $R^1$, with $R^4$ an alkylpolyalkyleneoxide bearing substituent selected from the group consisting of:
$R^{13}(C_2H_4O)_a(C_3H_6O)_b(C_4H_8O)_c R^{14}$ and
$R^{12}SiR^5R^6(R^{13}(C_2H_4O)_a(C_3H_6O)_b(C_4H_8O)_c R^{14})$
where $R^{13}$ is a divalent linear or branched hydrocarbon radical having the structure:
$-CH_2-CH(R^{15})(R^{16})_d O-$
where $R^{15}$ is H or methyl; $R^{16}$ is a divalent alkyl radical of 1 to 6 carbons where the subscript d may be 0 or 1;
$R^{14}$ is selected from the group consisting of H, monovalent hydrocarbon radicals of from 1 to 6 carbon atoms and acetyl subject to the limitation that the subscripts a, b and c are zero or positive and satisfy the following relationships:

$2 \leq a+b+c \leq 20$ with $a \geq 2$, and $R^5$ and $R^6$ are each independently selected from the group of monovalent hydrocarbon radicals having from 1 to 6 carbon atoms or $R^4$. When the subscript a satisfies the condition $2 \leq a \leq 4$ it is advisable to utilize a cosurfactant as hereinafter set forth in order to obtain the benefit of the compositions of the present invention.

One method of producing the composition of the present invention is to react a molecule of the following formula:

$MM^H$ where $M^H$ is the hydride precursor to the M' structural unit in the composition of the present invention, wherein the definitions and relationships are later defined and consistent with those defined above, under hydrosilylation conditions, with an olefinically modified polyalkyleneoxide, such as allyloxy-polyethyleneglycol, or methallyloxypolyalkyleneoxide, which are incorporated herein as examples, and not set forth to limit other possible olefinically modified alkyleneoxide components. As used herein the phrase "olefinically modified polyalkyleneoxide" is defined as a molecule possessing one or more alkyleneoxide groups containing one or more, terminal or pendant, carbon-carbon double bonds. The polyether is an olefinically modified polyalkyleneoxide (hereinafter referred to as "polyether") is described by the general formula:

$$CH_2\!=\!CH(R^{15})(R^{16})_dO(C_2H_4O)_a(C_3H_6O)_b(C_4H_8O)_cR^{14}$$

where $R^{15}$ is H or methyl; $R^{16}$ is a divalent alkyl radical of 1 to 6 carbons where the subscript d may be 0 or 1; $R^{14}$ is H, a monofunctional hydrocarbon radical of 1 to 6 carbons, or acetyl. When the polyether is composed of mixed oxyalkyleneoxide groups (i.e. oxyethylene, oxypropylene and oxybutylene) the units may be blocked, or randomly distributed. One skilled in the art will understand the advantages of using a blocked or random configuration. Illustrative examples of blocked configurations are: -(oxyethylene)$_a$(oxypropylene)$_b$-; -(oxybutylene)$_c$(oxyethylene)$_a$-; and -(oxypropylene)$_b$(oxyethylene)$_a$(oxybutylene)$_c$-

Illustrative examples of the polyether are provided below, but not limited to:

$CH_2\!=\!CHCH_2O(CH_2CH_2O)_8H$; $CH_2\!=\!CHCH_2O(CH_2CH_2O)_8CH_3$;
$CH_2\!=\!CHCH_2O(CH_2CH_2O)_4(CH_2CH(CH_3)O)_5H$;
$CH_2\!=\!CHO(CH_2CH_2O)_5(CH_2CH(CH_3)O)_5H$;
$CH_2\!=\!C(CH_3)CH_2O(CH_2CH_2O)_4(CH_2CH(CH_3)O)_5C(\!=\!O)CH_3$;
$CH_2\!=\!CHCH_2O(CH_2CH_2O)_5(CH_2CH(CH_3)O)_2(CH_2CH(CH_2CH_3)O)_2H$

Polyether modified siloxanes are prepared in the normal manner through the use of a hydrosilylation reaction to graft the olefinically modified (i.e. vinyl, allyl or methallyl) polyalkyleneoxide onto the hydride (SiH) intermediate of the disiloxane of the present invention.

Precious metal catalysts suitable for making polyether-substituted siloxanes are also well known in the art and comprise complexes of rhodium, ruthenium, palladium, osmium, iridium, or platinum. Many types of platinum catalysts for this SiH olefin addition reaction are known and such platinum catalysts may be used to generate the compositions of the present invention. The platinum compound can be selected from those having the formula (PtCl$_2$Olefin) and H(PtCl$_3$Olefin) as described in U.S. Pat. No. 3,159,601, hereby incorporated by reference. A further platinum containing material can be a complex of chloroplatinic acid with up to 2 moles per gram of platinum of a member selected from the class consisting of alcohols, ethers, aldehydes and mixtures thereof as described in U.S. Pat. No. 3,220,972 hereby incorporated by reference. Yet another group of platinum containing materials useful in this present invention is described in U.S. Pat. Nos. 3,715,334; 3,775,452 and 3,814,730 (Karstedt). Additional background concerning the art may be found in J. L. Spier, "Homogeneous Catalysis of Hydrosilation by Transition Metals", in Advances in Organometallic Chemistry, volume 17, pages 407 through 447, F.G.A. Stone and R. West editors, published by Academic Press (New York, 1979). Those skilled in the art can easily determine an effective amount of platinum catalyst. Generally an effective amount ranges from about 0.1 to 50 parts per million of the total organomodified disiloxane composition.

The compositions as well as the siloxanes of the present invention exhibit an enhanced resistance to hydrolysis outside a pH range ranging from 6 to 7.5, i.e. in extreme environmental conditions. An extreme environment is defined as an aqueous solution pH below 6 or above 7.5 or non-aqueous equivalents in terms of Bronsted acidity or basicity or Lewis acidity ort basicity. Enhanced resistance to hydrolysis can be demonstrated by a variety of tests but as used herein enhanced resistance to hydrolysis means 50 mole percent or more of the hydrolysis resistant composition of the present invention remains unchanged or unreacted after a period of a twenty-four exposure to aqueous acidic conditions where the solution has a pH lower than 6 or after a period of a twenty-four hour exposure to aqueous basic conditions where the solution has a pH greater than 7.5. Under acidic conditions the compositions of the present invention show a survival of 50 mole percent of the original concentration or greater at a pH of 5 or less for a period of time in excess of 48 hours; specifically the compositions of the present invention show a survival of 50 mole percent or greater at a pH of 5 or less for a period of time in excess of 2 weeks; more specifically the compositions of the present invention show a survival of 50 mole percent or greater at a pH of 5 or less for a period of time in excess of 1 month; and most specifically the compositions of the present invention show a survival of 50 mole percent or greater at a pH of 5 or less for a period of time in excess of 6 months. Under basic conditions the compositions of the present invention show a survival of 50 mole percent or greater at a pH of 8 or more for a period of time in excess of 2 weeks; specifically the compositions of the present invention show a survival of 50 mole percent or greater at a pH of 8 or more for a period of time in excess of 4 weeks; more specifically the compositions of the present invention show a survival of 50 mole percent or greater at a pH of 8 or more for a period of time in excess of 6 months; and most specifically the compositions of the present invention show a survival of 50 mole percent or greater at a pH of 8 or more for a period of time in excess of 1 year.

Uses for the Compositions of the Present Invention:

The compositions of the present invention may be utilized in a variety of forms: as liquid solutions, dispersions of solids in liquids, dispersions of liquids in liquids as the previously described emulsions, solid mixtures or solid solutions either separately or in the forms previously listed in combination one with the other.

A. Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications. The pesticidal compositions of the present invention also include at least one pesticide, where the organomodified disiloxane surfactant of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticides, including larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and Micronutrients:

Fertilizers or micronutrients include, but are not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride.

The pesticide or fertilizer may be a liquid or a solid. If a solid, it is preferable that it is soluble in a solvent, or the organomodified disiloxanes of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1-3-pentane diol and alkoxylated (especially ethoxylated) versions thereof as illustrated in U.S. Pat. No. 5,674,832 herein incorporated by reference, or n-methyl-pyrrilidone.

Cosurfactants:

Cosurfactants useful herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL-Air Products), pyrrilodone based surfactants (e.g., SURFADONE-LP 100-ISP), 2-ethyl hexyl sulfate, isodecyl alcohol ethoxylates (e.g., RHODASURF DA 530-Rhodia), ethylene diamine alkoxylates (TETRONICS-BASF), ethylene oxide/propylene oxide copolymers (PLURONICS-BASF), Gemini type surfactants (Rhodia) and diphenyl ether Gemini type surfactants (e.g. DOWFAX-Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Tenn.), modified clays such as Surround® (Englehard Corp.), foam control agents, surfactants, wetting agents, dispersants, emulsifiers, deposition aids, anti-drift components, and water.

Suitable agrochemical compositions are made by combining, in a manner known in the art, such as, by mixing one or more of the above components with the organomodified disiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

B. Coatings:

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as, Solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, alkyds, acrylics, epoxies and polyurethanes.

C. Personal Care

In a preferred embodiment, the organomodified disiloxane surfactant of the present invention comprises, per 100 parts by weight ("pbw") of the personal care composition, from 0.1 to 99 pbw, more preferably from 0.5 pbw to 30 pbw and still more preferably from 1 to 15 pbw of the organomodified disiloxane surfactant and from 1 pbw to 99.9 pbw, more preferably from 70 pbw to 99.5 pbw, and still more preferably from 85 pbw to 99 pbw of the personal care composition.

The organomodified disiloxane surfactant compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and, when sufficiently small, microemulsions may be transparent. Further it is also possible to prepare emulsions of emulsions and these are generally known as multiple emulsions. These emulsions may be:

1) aqueous emulsions where the discontinuous phase comprises water and the continuous phase comprises the organomodified disiloxane surfactant of the present invention;

2) aqueous emulsions where the discontinuous phase comprises the organomodified disiloxane surfactant of the present invention and the continuous phase comprises water;

3) non-aqueous emulsions where the discontinuous phase comprises a non-aqueous hydroxylic solvent and the continuous phase comprises the organomodified disiloxane surfactant of the present invention; and 4) non-aqueous emulsions where the continuous phase comprises a non-aqueous hydroxylic organic solvent and the discontinuous phase comprises the organomodified disiloxane surfactant of the present invention.

Non-aqueous emulsions comprising a silicone phase are described in U.S. Pat. No. 6,060,546 and U.S. Pat. No. 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the organomodified disiloxane surfactant of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, volatile silicones, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the organomodified disiloxane surfactant. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the organomodified disiloxane surfactant of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrexgly.

In another useful embodiment, a skin care composition comprises the organomodified disiloxane surfactant, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the organomodified disiloxane surfactant, and a coloring agent, such as, a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions, other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

EXPERIMENTAL

The hydride intermediates for the organomodified disiloxane surfactant compositions of the present invention, as well as comparative compositions were prepared as described in the following examples.

Preparation Example 1

1-(2-trimethylsilylethyl)-1,1,3,3-tetramethyldisiloxane (Structure 1). A 250 mL round bottom flask was charged with tetramethyldisiloxane (51.6 g) and Wilkinson's catalyst ((PPh$_3$)$_3$RhCl, 100 ppm), stirred under N$_2$, and brought to 60° C. Trimethylvinylsilane (25.6 g) was charged to an addition funnel, added dropwise at a rate to maintain the reaction temperature <70° C. with cooling (~1 g/min). The reaction was maintained 1 h @ 65° C., then sampled for GC; found residual tetramethyldisiloxane and 94:6 M'M$^R$: M$^R$M$^R$). Resulting material distilled fractionally under vacuum (approx. 30 mm Hg) to yield 51.6 g M'M$^R$ product, 99.1% GC purity. This product was found to have an Si—H content of 96 cc H$_2$/g by gasiometric titration.

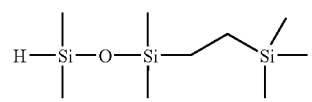

Structure 1

Preparation Example 2

1-(3,3-dimethylbutyl)-1,1,3,3-tetramethyldisiloxane (Structure 2). A 250 mL round bottom flask was charged with tetramethyldisiloxane (46.1 g), and stirred under N$_2$. A solution of Karstedt's catalyst (Pt(0) in divinyltetramethyldisiloxane, 10 ppm) in 3,3-dimethyl-1-butene (19.3 g) was charged to an addition funnel, and added dropwise at a rate to maintain the reaction temperature <40° C. with cooling (~0.5 g/min). The reaction was maintained 1 h @ 50° C., then sampled for GC; found residual tetramethyldisiloxane, M'M$^R$ product, and M$^R$M$^R$ byproduct (32:53:9). Resulting material distilled fractionally under vacuum (approx. 30 mm Hg) using a 25-cm Vigreux column to yield 25.0 g M'M$^R$ product, >98.1% GC purity. This product was found to have an Si—H content of 100 cc H$_2$/g by gasiometric titration.

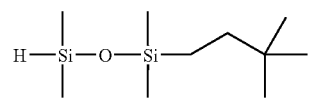

Structure 2

Preparation Example 3

1-(2-methylpropyl)-1,1,3,3-tetramethyldisiloxane (Structure 3). An 80 mL Fischer-Porter high pressure bottle was charged with tetramethyldisiloxane (10.0 g), toluene (10.0 g) and Wilkinson's catalyst ((PPh$_3$)$_3$RhCl, 40 ppm), stirred and brought to 60° C. The bottle was attached to a manifold and pressurized with isobutylene (25 psig) and maintained at 60-70° C. for 8 h. The pressure was vented, and the reaction was sampled for GC analysis; found residual tetramethyldisiloxane, M'MR product and MRMR byproduct (2:95:3). The resulting material was stripped under vacuum (approx. 150 mm Hg) at 40° C. to remove olefin and M'M', then filtered with Celite to yield 21.3 g M'M$^R$ product/toluene solution, 94% GC purity. This product was found to have an Si—H content of 11 cc H$_2$/g by gasiometric titration.

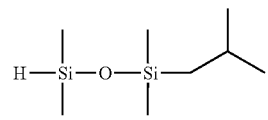

Structure 3

Preparation Example 4

1-propyl-1,1,3,3-tetramethyldisiloxane (Structure 4). An 80 mL Fischer-Porter high pressure bottle was charged with tetramethyldisiloxane (10.0 g), toluene (10.0 g) and Wilkinson's catalyst ((PPh$_3$)$_3$RhCl, 40 ppm), stirred and brought to 50° C. The bottle was attached to a manifold and pressurized with propylene (40 psig) and maintained at 50° C. for 2 h. The pressure was vented, and the reaction was sampled for GC analysis; found M'M$^R$ product and M$^R$M$^R$ byproduct (40:60). The resulting mixture of materials was used without further purification, yield 140.1 g.

Structure 4

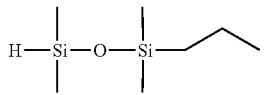

Preparation Example 5

1-tert-butyl-1,1,3,3-tetramethyldisiloxane (Structure 5). A 1 L round bottom flask was charged with water (95 g) and diisopropyl ether (50 g) and stirred. A solution of tert-butyldimethylsilyl chloride (39.5 g) in isopropyl ether (50 g) was charged to an addition funnel, and added dropwise to the water/IPE mixture at a rate to maintain the reaction temperature between 30-35° C. After complete addition, the reaction temperature was brought to 40° C. and maintained for 1 h. A solution of dimethylchlorosilane (24.8 g) in isopropyl ether (50 g) was then charged to the addition funnel, and this solution was added dropwise at 40-45° C. After complete addition, the reaction mixture was heated to reflux for 1 h and allowed to cool. After aqueous workup (washing with water and aqueous NaHCO$_3$, and drying organic fractions over MgSO$_4$), the product was isolated by fractional distillation under vacuum to yield 39.2 g M(R)M' product/isopropyl ether solution (70%/20% by GC analysis). This product was found to have an Si—H content of 79 cc H$_2$/g by gasiometric titration.

Structure 5

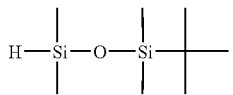

Preparation Example 6

1-(dicyclopentadienyl)-1,1,3,3-tetramethyldisiloxane (Structure 6). A 250 mL RBF was charged with tetramethyldisiloxane (45.3 g), stirred under N$_2$, and brought to 40° C. A solution of Karstedt's catalyst (Pt(0) in divinyltetamethyldisiloxane, 40 ppm) in dicyclolpentadiene (29.8 g) was charged to an addition funnel, and added dropwise at a rate to maintain the reaction temperature <60° C. with cooling (~0.5 g/min). After complete addition, the reaction was maintained 1 h @ 60° C. The reaction mixture was stripped in vacuo (~30 mm Hg) at 100° C. to yield 41.1 g M'M$^R$ product, >96% GC purity. This product was found to have an Si—H content of 81 cc H$_2$/g by gasiometric titration.

Structure 6

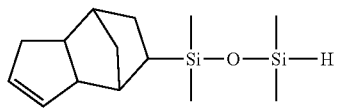

Preparation Example 7

The hydride intermediates of Examples 1-6 were further modified with various allylpolyalkyleneoxides to yield the organomodified disiloxane compositions of this instant invention (From Examples 1, 2, 3 and 5), as well as the comparative disiloxane surfactants (From Examples 4 and 6).

Additionally comparative trisiloxane alkoxylates were prepared by conventional methods of platinum mediated hydrosilation, as described in Bailey, U.S. Pat. No. 3,299,112, herein incorporated by reference.

Table 1 provides a description of the compositions of the present invention. These compositions are described by the general structure:

M*M'' where M*=R$^1$Si(CH$_3$)$_2$O$_{0.5}$; M''=O$_{0.5}$Si(CH$_3$)$_2$Q
where R$^1$ is described in Table 2;
Q=—CH$_2$CH$_2$CH$_2$O(CH$_2$CH$_2$O)$_a$(CH$_2$CH(CH$_3$)O)$_b$R$^2$

TABLE 1

Description of Organomodified Disiloxane Surfactant Compositions

| I.D. | R$^1$ | a | b | R$^2$ |
|---|---|---|---|---|
| 1 | (CH$_3$)$_2$CHCH$_2$— | 7.5 | 0 | CH$_3$ |
| 2 | CH$_3$CH$_2$CH$_2$— | 7.5 | 0 | CH$_3$ |
| 3 | (CH$_3$)$_2$CHCH$_2$— | 7.5 | 0 | H |
| 4 | (CH$_3$)$_2$CHCH$_2$— | 11 | 0 | H |
| 5 | (CH$_3$)$_3$C— | 7.5 | 0 | CH$_3$ |
| 6 | (CH$_3$)$_2$CHCH$_2$— | 7.5 | 0 | H |
| 7 | (CH$_3$)$_2$CHCH$_2$— | 11 | 0 | H |
| 8 | (CH$_3$)$_2$CHCH$_2$— | 7.5 | 0 | CH$_3$ |
| 9 | (CH$_3$)$_3$SiCH$_2$CH$_2$— | 7.5 | 0 | H |
| 10 | (CH$_3$)$_3$SiCH$_2$CH$_2$— | 7.5 | 0 | CH$_3$ |
| 11 | (CH$_3$)$_3$SiCH$_2$CH$_2$— | 11 | 0 | H |
| 12 | (CH$_3$)$_3$SiCH$_2$CH$_2$— | 5 | 2.5 | H |
| 13 | (CH$_3$)$_3$SiCH$_2$CH$_2$— | 6.3 | 0 | H |

TABLE 2

Comparative Siloxane Based Surfactants

| I.D. | R$^1$ | a | b | R$^2$ |
|---|---|---|---|---|
| A | CH$_3$— | 7.5 | 0 | H |
| B | CH$_3$— | 7.5 | 0 | CH$_3$ |
| C | CH$_3$— | 11 | 0 | H |
| D | (dicyclopentadienyl) | 11 | 0 | H |
| H | (dicyclopentadienyl) | 7.5 | 0 | H |

Table 3 provides a description of the comparative organosilicone polyether based surfactants of the general structure:

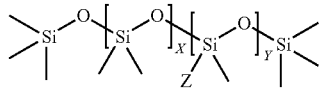

where Z=—CH$_2$CH$_2$CH$_2$O(CH$_2$CH$_2$O)$_a$(CH$_2$CH(CH$_3$)O)$_b$R$^2$

TABLE 3

Composition of Comparative Organosilicone Polyether Surfactants

| I.D. | x | y | Z Group a | b | $R^2$ |
|---|---|---|---|---|---|
| E | 0 | 1 | 7.5 | 0 | $CH_3$ |
| F | 0 | 1 | 7.5 | 0 | H |
| G | 20 | 3 | 7.5 | 0 | $CH_3$ |

Additionally, comparative sample OPE (Octylphenolethoxylate, containing 10 polyoxyethylene units) is a non-silicone organic surfactant. This product is available as Triton® X-100 from Dow Chemical Company, Midland, Mich.

Example 8

This example demonstrates the ability of the organomodified disiloxane composition of the present invention to reduce aqueous surface tension thereby showing utility as surfactants. Surface tension was measured using a Kruss surface tensiometer, with a sand blasted platinum blade as the sensor. Solutions of the various components were prepared at 0.1 wt % in 0.005M NaCl water (Deionized), as an equilibrium aid.

Table 4 shows that solutions of these unique compositions provide a significant reduction in surface tension relative to the conventional surfactant.

The compositions of the present invention also provide spreading properties similar to the TSAs (E and F), and comparative disiloxane surfactants (A, B, C, D and H). Additionally, organomodified disiloxane surfactants of the present invention provide improved spreading relative to the conventional silicone polyether (G) and conventional organic surfactant product OPE (Table 4).

Spreading was determined by applying a 10 µL droplet, of surfactant solution to polyacetate film (USI, "Crystal Clear Write on Film") and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 4

Surface Tension and Spreading Properties

| I.D. | Surface Tension mN/m | Spread Diameter (mm) 0.1% | 0.2% | 0.4% |
|---|---|---|---|---|
| 1 | 23.3 | 40 | 42 | 50 |
| 2 | 23.6 | 34 | 36 | 33 |
| 3 | 24.0 | 12 | 14 | 24 |
| 4 | 24.1 | 8 | 9 | 10 |
| 5 | 23.5 | 32 | 48 | 45 |
| 6 | 23.2 | 41 | 33 | 23 |
| 7 | 23.9 | 14 | 15 | 25 |
| 8 | 24.0 | 23 | 33 | 41 |
| 9 | 22.8 | 14 | 25 | 49 |
| 10 | 23.0 | 15 | 27 | 34 |
| 11 | 24.5 | 20 | 21 | 32 |
| 12 | 24.3 | 7 | 8 | 10 |
| 13 | 22.2 | 14 | 32 | 27 |
| A | 23.4 | 8 | 36 | 58 |
| B | 24.3 | 8 | 12 | 44 |
| C | 24.1 | 6 | 8 | 9 |
| D | 32.7 | 7 | nd | nd |
| E | 20.9 | 53 | 51 | 25 |
| F | 20.6 | 53 | 50 | 35 |
| G | 23.6 | nd | nd | 6 |
| H | nd | nd | nd | 7 |
| OPE | 31.8 | nd | nd | 10 |

Example 9

Hydrolytic stability was determined for representative compositions of the present invention using HPLC. Solutions of the various compositions were prepared at 0.5 wt % over a pH range from pH 4 to pH12, and monitored by HPLC for decomposition as a function of time.

Analytical Method:

The samples were analyzed by a reverse-phase chromatographic technique using the experimental conditions listed in Table 5.

TABLE 5

Solvent Gradient for HPLC Method

| Time (min.) | % Methanol | % Water | % Isopropanol |
|---|---|---|---|
| 0.0 | 70 | 30 | 0 |
| 15.0 | 100 | 0 | 0 |
| 20.0 | 50 | 0 | 50 |
| 20.1 | 70 | 30 | 0 |
| 25.0 | 70 | 30 | 0 |

Detector: ELSD/LTA (Evaporative Light Scattering with Low Temperature Adapter

Conditions: 30° C., 1.95 SLPM $N_2$

Column: Phenomenex LUNA C18 end cap, 5 micron, 75×4.6 mm

Flow Rate: 1.0 mL/min.

Inj. Volume: 10 microlitres

Sample: 0.050 g/mL in methanol

Tables 6-16 demonstrates that the compositions of the present invention provide improved resistance to hydrolytic decomposition relative to the standard comparative siloxane-based surfactants siloxanes B and E under similar pH conditions.

Comparative siloxanes B and E show rapid hydrolysis at ≦pH5 and >pH 7, while the organomodified disiloxane surfactants of the present invention demonstrate a higher resistance to hydrolysis under the same conditions.

Although comparative D shows similar resistance to hydrolysis, it does not provide the enhanced spreading properties associated with the organomodified disiloxane surfactants of the present invention. For example comparative D gave a spread diameter of only 6 mm (0.4%) and had 82% product remaining by HPLC, after 48 h at pH4, while the organomodified disiloxane surfactant product 10 gave a spread diameter of 34 mm and maintained 75% product after 1 week, under the same conditions (Tables 4, 11 and 16).

TABLE 6

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 1 | 24 h | 83 | 100 | 100 | 100 | 100 | 100 | nd |
|   | 1 wk | 8 | 71 | 100 | 100 | 100 | 68 | nd |
|   | 2.5 wk | 1 | 38 | 100 | 100 | 83 | 35 | nd |
|   | 15 wk | 0.5 | 4 | 100 | 100 | 42 | 28 | nd |

TABLE 7

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 2 | 24 h | 23 | 88 | 100 | 100 | 100 | 79 | nd |
|   | 1 wk | 1 | 26 | 100 | 95 | 69 | 17 | nd |
|   | 2.5 wk | 0 | 7 | 100 | 89 | 44 | 7 | nd |

TABLE 8

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 5 | 1 wk | 65 | 100 | 100 | 100 | 100 | 100 | nd |
|   | 4 wk | 32 | 76 | 100 | 100 | 100 | 100 | nd |
|   | 6 wk | 21 | 64 | 100 | 100 | 100 | 100 | nd |

TABLE 9

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 8 | 24 h | 84 | 100 | 100 | 100 | 100 | nd | nd |
|   | 1 wk | 50 | 100 | 100 | 100 | 100 | nd | nd |
|   | 2 wk | 31 | 79 | 100 | 100 | 100 | nd | nd |
|   | 4 wk | 21 | 65 | 100 | 97 | 88 | nd | nd |
|   | 10 wk | 7 | 45 | 100 | 93 | 83 | nd | nd |

TABLE 10

Hydrolytic Stability of Siloxane Based Surfactants by HPLC

Stability: % Siloxane Surfactant Remaining

| I.D | Time | pH 4 | pH 5 | pH 7 | pH 9 | pH 10 | pH 11 | pH 12 |
|---|---|---|---|---|---|---|---|---|
| 9 | 24 h | 92 | 100 | 100 | 100 | 100 | nd | nd |
|   | 1 wk | 67 | 100 | 100 | 100 | 100 | nd | nd |

TABLE 11

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 10 | 24 h | 100 | 100 | 100 | 100 | 100 | 100 | 79 |
|    | 1 wk | 75 | 100 | 100 | 100 | 100 | 93 | 42 |
|    | 2 wk | 50 | 88 | 100 | 100 | 100 | nd | nd |
|    | 3 wk | 32 | 80 | 100 | 100 | 100 | 93 | 34 |
|    | 7 wk | nd | nd | nd | nd | nd | 93 | 11 |
|    | 7.5 wk | 12 | 56 | 100 | 100 | 100 | nd | nd |
|    | 11 wk | nd | 48 | 100 | 100 | 100 | nd | nd |
|    | 13 wk | nd | nd | nd | nd | nd | 95 | nd |
|    | 17 wk | nd | nd | 100 | 100 | 84 | nd | nd |
|    | 27 wk | nd | nd | 100 | 100 | 86 | 100 | nd |

TABLE 12

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 11 | 96 h | 100 | 100 | 100 | 100 | 100 | nd | nd |
|    | 3 wk | 79 | 100 | 100 | 100 | 100 | nd | nd |
|    | 6 wk | 56 | 100 | 100 | 100 | 100 | nd | nd |
|    | 11 wk | 10 | 100 | 100 | 100 | 100 | nd | nd |

Note:
Stock Solution 2.5 wt %

TABLE 13

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| 13 | 24 h | 100 | 100 | 100 | 100 | 100 | nd | nd |
|    | 1 wk | 56 | 100 | 100 | 100 | 100 | nd | nd |

TABLE 14

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| E | 48 h | 25 | 100 | 100 | 100 | 46 | nd | nd |
|   | 1 wk | 0 | 38 | 100 | 53 | 0 | nd | nd |

TABLE 15

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| B | 24 h | 0 | 0 | 100 | 38 | 0 | nd | nd |

TABLE 16

Hydrolytic Stability of Siloxane Based Surfactants by HPLC

Stability: % Siloxane Surfactant Remaining

| I.D. | Time | pH 4 | pH 5 | pH 7 | pH 9 | pH 10 | pH 11 | pH 12 |
|---|---|---|---|---|---|---|---|---|
| D | 48 h | 82 | >95 | >95 | >95 | >95 | nd | nd |
|   | 9 days | 44 | 99 | 99 | 99 | 99 | nd | nd |

Examples 10-12

Unlike traditional siloxane based surfactants, which are subject to rapid hydrolysis under acidic and basic conditions ($\leq$pH 5 and $\geq$pH 9) the organomodified disiloxane surfactants of the present invention provide increased resistance to hydrolysis relative to traditional trisiloxane alkoxylates (Comparative E and F), as well as the comparative trimethylsilyl terminated disiloxane surfactants, represented by Comparative B. An artifact of hydrolysis is observed as a reduction in superpsreading properties over time. Therefore solutions of the organomodified disiloxane surfactants of the present invention, as well as comparative surfactants were prepared at desired use levels and pH. Spreading was determined as a function of time to illustrate resistance to hydrolysis.

Example 10

Table 17 is an illustrative example of the organomodified disiloxane surfactants, where product No. 10, has improved resistance to hydrolysis, at pH 3, relative to a traditional trisiloxane ethoxylate superspreading surfactant (Product E). As mentioned above, resistance to hydrolysis was observed by monitoring the spreading properties over time. Here a 0.4 wt % solution was prepared at pH 3, and spreading determined according to the procedure in Example 8.

TABLE 17

Spreading Properties at pH 3 vs Time (h)

Time/Spread Diameter (mm)

| I.D | 0 h | 0.25 h | 0.5 h | 1 h | 2 h | 4 h | 8 h | 24 h | 32 h | 96 h |
|---|---|---|---|---|---|---|---|---|---|---|
| 10 | 32 | 39 | 41 | 49 | 48 | 39 | 39 | 36 | 16 | 19 |
| E | 48 | 48 | 43 | 42 | 44 | 12 | 12 | 9 | — | — |

Example 11

In another example the organomodified disiloxane surfactants of the present invention represented by product Nos. 6 and 11, demonstrate improved resistance to hydrolysis relative to product F, a trisiloxane ethoxylate superspreader (Table 18). Solutions (0.4 wt %) of the surfactants were prepared at pH 4 and pH 5 and spreading properties were observed over time. The test conditions are outlined in Example 8.

TABLE 18

Spreading Properties at pH 4 and pH 5 Vs Time

Spreading Diameter (mm)
ID:

| Time | 6 pH 4 | 6 pH 5 | 11 pH 4 | 11 pH 5 | F pH 4 | F pH 5 |
|---|---|---|---|---|---|---|
| 0 h | 50 | 46 | 16 | 26 | 50 | 49 |
| 1 h | 48 | 44 | 23 | 23 | 50 | 50 |
| 4 h | 59 | 48 | 23 | — | 46 | 47 |
| 24 h | 49 | 51 | 44 | 24 | 52 | 51 |
| 48 h | 40 | 49 | 38 | 32 | 39 | 49 |
| 72 h | 42 | 50 | 28 | 35 | 16 | 48 |
| 1 wk | 13 | 43 | 8 | 29 | 12 | 52 |
| 2 wk | 11 | 49 | 8 | 33 | 7 | 53 |
| 3 wk | 18 | 47 | 12 | 33 | 6 | 21 |
| 1 mo | 17 | 49 | 10 | 42 | 6 | 15 |

Example 12

In another example the organomodified disiloxane surfactants of the present invention, represented by product No. 5, shows improved resistance to hydrolysis relative to comparative product E. Here surfactant solutions (0.1 wt %) were prepared at pH 4, pH 5, pH 8, pH 9 and pH 10, and the spreading properties over time were observed as described in Example 8.

Table 19 demonstrates that the comparative silicone E shows a more rapid loss of spreading properties at pH 4, pH 5, pH 9 and pH 10, than product No. 5.

TABLE 19

Spreading Properties vs. Time

Spread Diameter (mm)

| Time | Product | pH 4 | pH 5 | pH 8 | pH 9 | pH 10 |
|---|---|---|---|---|---|---|
| 0 h | 5 | 53 | 52 | 52 | 51 | 51 |
|     | E | 56 | 54 | 56 | 54 | 54 |
| 1 h | 5 | 52 | 50 | 51 | 50 | 51 |
|     | E | 55 | 53 | 53 | 56 | 54 |
| 2 h | 5 | 54 | 52 | 50 | 49 | 50 |
|     | E | 51 | 53 | 55 | 55 | 52 |
| 4 h | 5 | 51 | 50 | 50 | 48 | 49 |
|     | E | 41 | 51 | 56 | 53 | 49 |
| 6 h | 5 | 51 | 50 | 50 | 48 | 49 |
|     | E | 35 | 52 | 50 | 53 | 46 |
| 8 h | 5 | 48 | 51 | 52 | 49 | 52 |
|     | E | 29 | 50 | 51 | 51 | 47 |
| 24 h | 5 | 51 | 50 | 52 | 51 | 49 |
|      | E | 7 | 50 | 53 | 50 | 32 |
| 48 h | 5 | 39 | 48 | 46 | 46 | 41 |
|      | E | 6 | 41 | 47 | 43 | 10 |
| 72 h | 5 | 33 | 48 | 45 | 45 | 42 |
|      | E | 6 | 32 | 49 | 44 | 7 |
| 96 h | 5 | 23 | 45 | 47 | 46 | 40 |

TABLE 19-continued

Spreading Properties vs. Time

| Time | Product | Spread Diameter (mm) | | | | |
|---|---|---|---|---|---|---|
| | | pH 4 | pH 5 | pH 8 | pH 9 | pH 10 |
| | E | 6 | 17 | 50 | 41 | 6 |
| 168 h | 5 | 8 | 43 | 43 | 44 | 43 |
| | E | 5 | 9 | 50 | 32 | 6 |

Example 13

The impact of other ingredients on spreading was determined by blending the organosilicone disiloxane surfactant of the present invention, with a conventional organic based cosurfactant. The cosurfactants are described in Table 20.

Blends were prepared as physical mixtures where the weight fraction silicone is represented by α (alpha), indicating that the cosurfactant makes up the balance of the blend ratio. For example when α=0 this indicates that the composition contains 0% of the silicone component and 100% cosurfactant, while an α=1.0 indicates the composition contains 100% silicone, and no (0%) cosurfactant. Mixtures of the two components are represented by the weight fraction α, where α ranges as follows: 0≦α≦1.0. By example when α=0.25 this indicates the surfactant mixture is composed of 25% silicone and 75% cosurfactant. These blends are then diluted in water to the desired concentration for spreading evaluation.

Spreading was determined as described in Example 8, at either 0.1 wt % or 0.2 wt % total surfactant.

Table 21 demonstrates that representative examples of the cosurfactants of the present invention provide favorable spreading results, and in some cases provide an unexpected synergistic enhancement, where the spread diameter of the mixture exceeds that of the individual components.

TABLE 20

Description of Conventional Cosurfactants

| ID | Description |
|---|---|
| IDA-5 | Isodecyl alcohol ethoxylate (4-5 EO) |
| IDA-6 | Isodecyl alcohol ethoxylate (5-6 EO) |
| TMN-6 | Trimethylnonylalcohol ethoxylate (6 EO) |
| Oxo-TDA-5 | Oxo-tridecyl alcohol ethoxylate (5 EO) |
| Oxo-TDA-6 | Oxo-tridecyl alcohol ethoxylate (6 EO) |
| APG | $C_{8-10}$ Alkylpolyglucoside |

TABLE 21

Effect of Cosurfactants on Blend Spreading Properties

| Run | Silicone | Wt Fraction (α) Silicone Surfactant Spread diameter (mm) | | | | | Cosurfactant |
|---|---|---|---|---|---|---|---|
| | | 0 | 0.25 | 0.50 | 0.75 | 1.0 | |
| 1 | 10[a] | 45 | 49 | 23 | 17 | 25 | IDA-5 |
| 2 | 10[a] | 35 | 38 | 47 | 26 | 25 | IDA-6 |
| 3 | 10[a] | 41 | 38 | 42 | 36 | 25 | TMN-6 |
| 4 | 10[a] | 34 | 29 | 23 | 19 | 25 | Oxo-TDA-5 |
| 5 | 10[a] | 39 | 42 | 49 | 36 | 25 | Oxo-TDA-6 |
| 6 | 10[a] | 10 | 39 | 42 | 35 | 25 | APG |
| 7 | 5[b] | 41 | 46 | 47 | 49 | 50 | IDA-5 |
| 8 | 5[b] | 19 | 31 | 35 | 46 | 50 | IDA-6 |
| 9 | 5[b] | 34 | 38 | 44 | 45 | 50 | TMN-6 |
| 10 | 5[b] | 36 | 40 | 44 | 51 | 50 | Oxo-TDA-5 |
| 11 | 5[b] | 38 | 40 | 39 | 46 | 50 | Oxo-TDA-6 |
| 12 | 5[b] | 8 | 32 | 40 | 48 | 50 | APG |

[a] = 0.2 wt % total surfactant
[b] = 0.1 wt % total surfactant

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. Such ranges may be viewed as a Markush group or groups consisting of differing pairwise numerical limitations which group or groups is or are fully defined by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

The invention claimed is:

1. An agricultural composition comprising:
a) a silicone having the formula:

MM' where
M=$R^1R^2R^3SiO_{1/2}$;
M'=$R^4R^5R^6SiO_{1/2}$;
with $R^1$ selected from the group consisting of branched monovalent hydrocarbon radical of from 3 to 6 carbon atoms and $R^7$, where $R^7$ is selected from the group consisting of $R^8R^9R^{10}SiR^{12}$ and $(R^4R^5R^6)SiR^{12}$
with $R^8$, $R^9$, and $R^{10}$ each independently selected from the group of monovalent hydrocarbon radicals having from 1 to 6 carbon atoms and monovalent aryl or alkaryl hydrocarbon radicals having from 6 to 13 carbon atoms and $R^{12}$ is a divalent hydrocarbon radical having from 1 to 3 carbon atoms,
$R^2$ and $R^3$ are each independently selected from the group of from 1 to 6 carbon atom monovalent hydrocarbon radicals or $R^1$, with $R^4$ an alkylpolyalkyleneoxide of the general formula:

$$R^{13}(C_2H_4O)_a(C_3H_6O)_b(C_4H_8O)_cR^{14}$$

where $R^{13}$ is a divalent linear or branched hydrocarbon radical having the structure:

—$CH_2$—$CH(R^{15})(R^{16})_d O$— where $R^{15}$ is H or methyl; $R^{16}$ is a divalent alkyl radical of 1 to 6 carbons where the subscript d may be 0 or 1;

$R^{14}$ is selected from the group consisting of H, monovalent hydrocarbon radicals of from 1 to 6 carbon atoms and acetyl where the subscripts a, b and c are zero or positive and satisfy the following relationships:

$2 \leq a+b+c \leq 20$ with $a \geq 2$, and $R^5$ and $R^6$ are each independently selected from the group of monovalent hydrocarbon radicals having from 1 to 6 carbon atoms or $R^4$; and b) an agriculturally active component selected from the group consisting of pesticides, fungicides, insecticides, herbicides and fertilizers wherein said agricultural composition has an enhanced resistance to hydrolysis.

2. The composition of claim 1 where $R^1$ is iso-propyl.
3. The composition of claim 1 where $R^1$ is iso-butyl.
4. The composition of claim 1 where $R^1$ is tert-butyl.
5. The composition of claim 1 where $R^1$ is $R^7$ where $R^7$ has the formula:

$R^8 R^9 R^{10} SiR^{12}$ with $R^8$, $R^9$, and $R^{10}$ each methyl and $R^{12}$ is a divalent hydrocarbon radical having 2 carbon atoms.

6. The composition of claim 1 where $R^{15}$ is hydrogen.
7. The composition of claim 1 where $R^2$ is methyl.
8. The composition of claim 2 where $R^{15}$ is hydrogen.
9. The composition of claim 2 where $R^2$ is methyl.
10. The composition of claim 3 where $R^{15}$ is hydrogen.
11. The composition of claim 3 where $R^2$ is methyl.
12. The composition of claim 4 where $R^{15}$ is hydrogen.
13. The composition of claim 4 where $R^2$ is methyl.
14. The composition of claim 5 where $R^{15}$ is hydrogen.
15. The composition of claim 5 where $R^2$ is methyl.
16. An aqueous emulsion wherein a discontinuous phase comprises water and the continuous phase comprises the composition of claim 1.
17. An aqueous emulsion wherein a continuous phase comprises water and the discontinuous phase comprises the composition of claim 1.
18. A non-aqueous emulsion wherein a discontinuous phase comprises a non-aqueous hydroxylic solvent and the continuous phase comprises the composition of claim 1.
19. A non-aqueous emulsion wherein a continuous phase comprises a non-aqueous hydroxylic solvent and the discontinuous phase comprises the composition of claim 1.
20. The composition of claim 1 wherein the pesticide is selected from the group consisting of rodenticides, insecticides, miticides, fungicides, and herbicides.
21. The composition of claim 1 wherein the herbicide is selected from the group consisting of phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

* * * * *